United States Patent [19]

Nicholson et al.

[11] Patent Number: 4,497,320
[45] Date of Patent: Feb. 5, 1985

[54] SURGICAL BLADE UNIT

[75] Inventors: James E. Nicholson, Lincoln; James P. Ryan, Milton, both of Mass.

[73] Assignee: Rudolph Beaver, Inc., Waltham, Mass.

[21] Appl. No.: 466,203

[22] Filed: Feb. 14, 1983

[51] Int. Cl.³ ............................................. A61B 17/32
[52] U.S. Cl. .................................... 128/305; 128/304
[58] Field of Search ............... 128/305, 304, 751, 757, 128/753, 754, 317; 30/343, 340, 342, 329; 279/105

[56] References Cited

U.S. PATENT DOCUMENTS

| 3,080,653 | 3/1963 | Dolin | 30/329 X |
| 3,667,470 | 6/1972 | Rubin | 128/304 |
| 4,054,127 | 10/1977 | Milan et al. | 128/213 |
| 4,074,431 | 2/1978 | Beaver et al. | 30/353 |

FOREIGN PATENT DOCUMENTS

| 2849694 | 5/1979 | Fed. Rep. of Germany | 128/305 |
| 2848483 | 5/1979 | Fed. Rep. of Germany | 128/757 |
| 5469 | 2/1912 | United Kingdom | 30/343 |

OTHER PUBLICATIONS

"Celcon ® Acetal Copolymer Typical Properties", Celanese.
"Micro-Sharp ® System 75 ®", Rudolph Beaver, Inc.
"Catalog 200, Surgical Blades and Handles", Rudolph Beaver, Inc., p. 12.
"Blade Chart", Rudolph Beaver, Inc.

Primary Examiner—Michael H. Thaler

[57] ABSTRACT

A surgical blade unit for receiving substantial cutting load and adapted for use with a selected shaft-form handle that has, at its distal end, an axially aligned blade-unit receiving opening. The blade-unit includes a metal blade defining a working edge and a load-transmitting, axially elongated metal support shank extending from the edge, and a intermediate load-transferring member of synthetic resin permanently molded about a proximal portion of the shank and defining an attachment fitting adapted to engage in load-transferring relationship with the handle. The proximal portion of the shank extends through the intermediate member in the attachment fitting region and is permanently embedded therein to define an elongated, load-transferring interface therewith. The intermediate member has substantial tensile and shear strength and is constructed and arranged to receive via the attachment fitting the surgeon's forces on the handle, and to receive via the substantial load-transferring interface, forces from the proximal end of the shank attributable to the resistance encountered by the metal blade, the substance of the intermediate member being adapted to transfer the surgeon's forces to overcome the resistance forces while maintaining the blade in fixed relationship to said handle. In preferred aspects of the invention, the attachment fitting comprises cooperatively acting threads on the handle and a proximal portion of the intermediate member, the blade unit is in the form of an arthroscopic retrograde blade, the unit being sized to lie within a surgical cannula and having a working edge disposed for reverse cutting.

11 Claims, 12 Drawing Figures

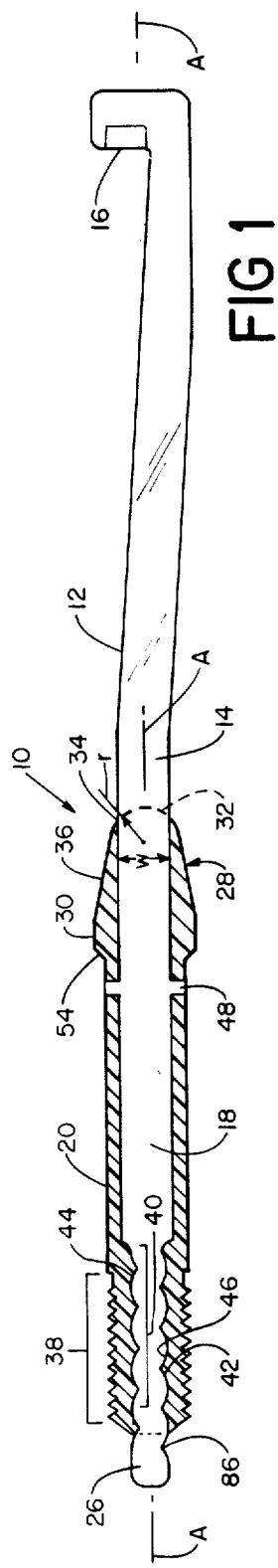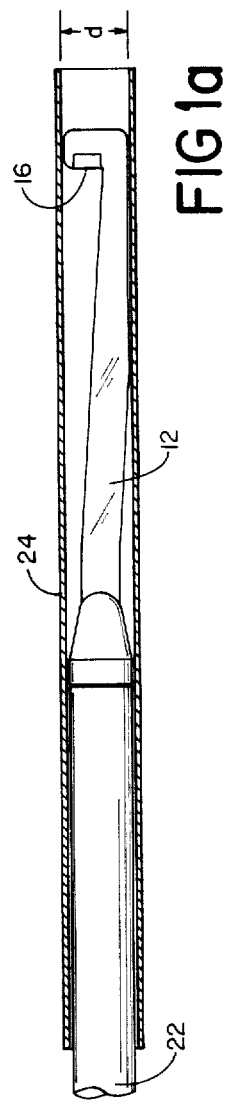

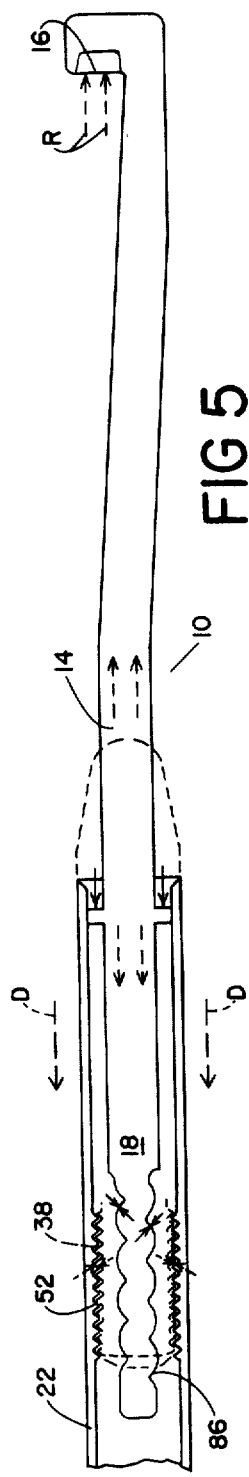
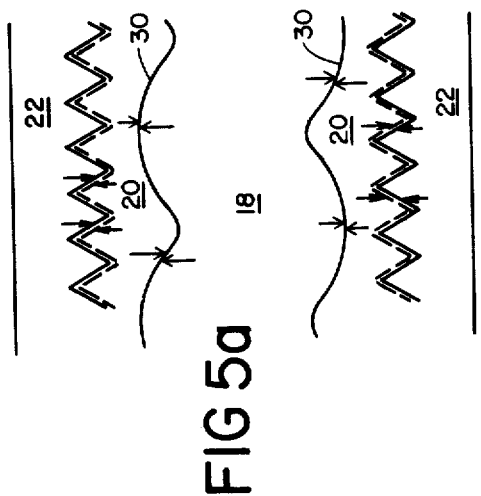
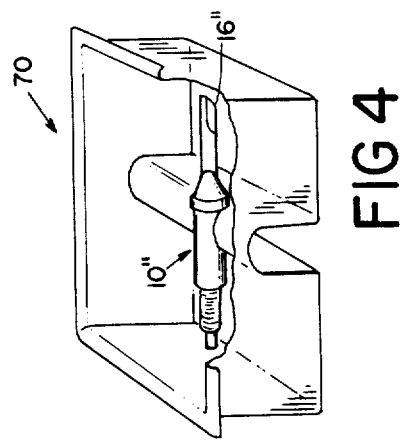

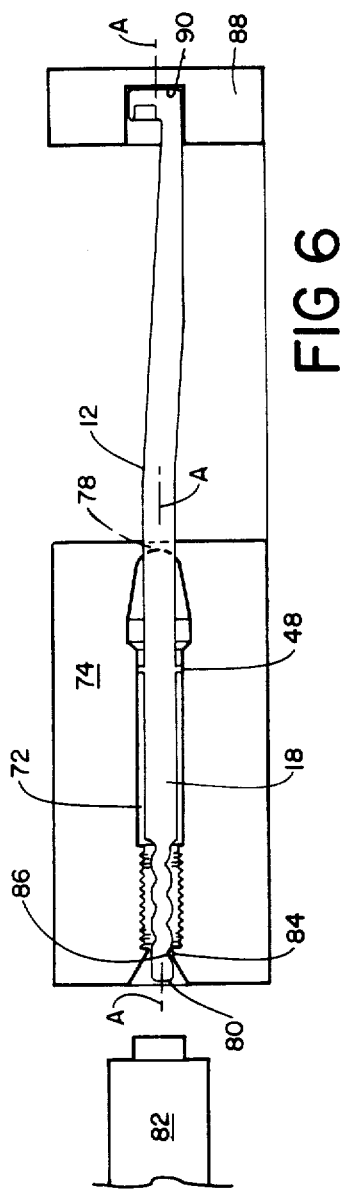
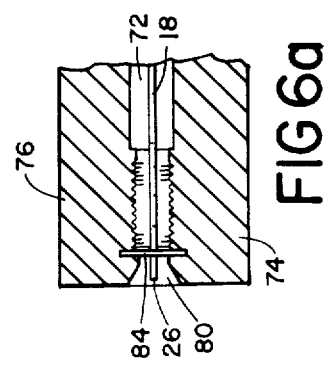

SURGICAL BLADE UNIT

BACKGROUND OF THE INVENTION

This invention relates to surgical blade units for use within the body and in particular to means for securing the portion of the device within the body against displacement from a handle under high force conditions.

It has long been recognized as desirable to employ handles and replaceable blade units in place of one-piece surgical scalpels to obtain the advantages of assured sharpness and sterility. Difficulties have been encountered in prior designs under high force conditions, especially where it is required that the unit be small. Particular problems have been encountered in arthroscopic surgery, i.e. surgery through a small puncture in the body in which the surgeon views the operative site by means of an arthroscope inserted via another puncture wound. The accidental detachment of a blade from a handle under such conditions is very undesirable.

The problem has perhaps been most serious with respect to reverse cutting involving pulling motions, such as retrograde scalpels in arthroscopic surgery.

SUMMARY OF THE INVENTION

According to the invention, a surgical blade unit for receiving substantial cutting load and adapted for use with a selected shaft-form handle that has, at its distal end, an axially aligned blade-unit receiving opening, comprises a metal blade defining a working edge and a load-transmitting, axially elongated metal support shank extending therefrom and an intermediate load-transferring member of synthetic resin permanently molded about a proximal portion of the shank, the distal extremity of the intermediate member being spaced proximally from the working edge leaving the blade and a substantial length of the distal portion of the shank exposed, a proximal portion of the intermediate member defining an attachment fitting adapted to engage in load-transferring relation with the handle, and the proximal portion of the shank extending through the intermediate member in the region of the attachment fitting and being permanently embedded within the intermediate molded member to define an elongated, load-transferring interface therewith. The intermediate member is comprised of synthetic resin that has substantial tensile and shear strength and is constructed and arranged to receive, via the attachment fitting, the surgeon's forces on the handle, and to receive via the substantial load-transferring interface, forces from the proximal end of the shank attributable to the resistance encountered by the metal blade, the substance of the intermediate member being adapted to transfer the surgeon's forces to overcome the resistance forces while maintaining the blade in fixed relationship to the handle.

According to one preferred aspect of the invention, the axially aligned blade-unit receiving opening in the handle is internally threaded, a distal portion of the intermediate member is terminated in a proximally directed, annular butt surface adapted to engage a distally directed surface of the handle, and a proximal portion of the intermediate member has a smaller diameter than the distal portion and defines a set of external threads adapted to match and engage in load-transferring relationship with internal threads of the handle.

In preferred embodiments of this preferred aspect of the invention, the body of the intermediate member is resiliently deformable to the degree that, without disturbing the load-transferring relationship of the intermediate member with the shank, hand tightening of the threads of the blade unit on the handle, and resultant compressional engagement of the annular butt surface of the intermediate member with the distal end surface of the handle, causes resilient stretching of the body of the intermediate member between the butt-surface and the external threads to produce a locking frictional engagement between these external threads and the internal threads of the handle, thereby to prevent rotation of the blade unit during surgical use.

In preferred embodiments of the invention, where the surgical blade unit is assembled with a selected shaft-form handle, the blade-unit receiving opening of the handle is configured to receive the attachment fitting portion of the blade unit in a close-fitting relationship, whereby the intermediate member is restricted against lateral expansion by the confining surfaces defining the opening; the blade unit is in the form of an arthroscopic blade, the blade and intermediate member being sized to lie within a surgical cannula of, e.g., 4 mm internal diameter; the blade unit is a retrograde blade, the working edge of the blade unit being disposed for operation during pulling motion; the synthetic resin is autoclavable and gamma irradiatable for sterilization, preferably the synthetic resin is selected from the group consisting of nylon, acetal copolymer, polysulfone; polyethylene and polypropylene and the distal end of the intermediate member is tapered to facilitate entry of the blade unit between close-lying portions of the body during surgery.

According to a further aspect of the invention, where the blade unit includes a retrograde blade, at the distal extremity of the intermediate member, the shank and intermediate member are substantially coaxial, the distal extremity of the shank supporting the working edge disposed for reverse cutting is substantially coaxial with the intermediate member, and the intervening exposed distal portion of the shank lies on an axis at an angle transverse to the axis of the intermediate member.

The invention thus provides a surgical blade unit which is simple, yet may be securely attached and locked to a variety of different handles for use under high force conditions, e.g. in the knee, and which is adapted to receive forces applied by the surgeon to overcome forces attributable to large resistances encountered by the blade, with markedly reduced danger of separation.

DESCRIPTION OF THE PREFERRED EMBODIMENT

We turn to the structure, use and manufacture of the preferred embodiment, first briefly describing the drawings.

DRAWINGS

FIG. 1 is a side view partially in section of a blade with a molded member according to the invention;

FIG. 1a is a side view partially in section of a different blade passing through a narrow diameter cannula into a surgical site;

FIG. 2 is a side view, partially in section, of a different blade unit inserted in a handle, while

FIG. 4 is an isometric view of an insert according to the invention in the holder package;

FIG. 5 is a free body diagram showing transfer of opposing forces applied during use, while FIG. 5a is a similar view enlarged to show lateral forces present in the assembled unit; and FIG. 6 is a top view of a mold part with a retrograde blade blank and mold insert in place according to the invention, while FIG. 6a is a side section view of the assembled mold for injection of synthetic resin.

STRUCTURE

Figure 2:
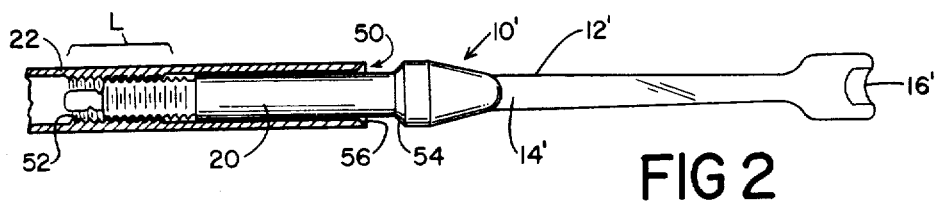

In FIG. 1, there is shown a surgical blade unit 10 adapted for use with a selected shaft-form handle in high force conditions, comprising blade 12, in this case a retrograde blade with elongated metal shank 14 having a sharpened working edge 16 adapted for reverse cutting, i.e. by pulling motion. Molded about proximal portion 18 of shank 14 is an intermediate load-transferring member 20 of rigid synthetic resin material, e.g. nylon, acetal, polysulfone, polyethylene or polypropylene selected for the characteristics discussed below. The blade unit 10 is sized and configured to allow passage through a narrow opening, e.g. for introduction on a handle 22 into the body through a small diameter, d, e.g. 3 to 5 mm, cannula 24, as shown in FIG. 1a, for arthroscopic surgery.

Shank 14, typically 2.3 inches in overall length, extends axially completely through member 20, with the distal end supporting working edge 16 exposed distally for a substantial length, typically about 1.2 inches for the retrograde blade shown, and end portion 26 projecting proximally from member 20, typically about 0.1 inch.

Intermediate member 20 has a bullet-shaped head portion 28 with maximum diameter, typically 0.16 inch, at the proximal annular surface 30, and terminates distally in hemisphere 32 of radius, r, typically about 0.055 inch, which is substantially equal to one half the width, W, typically about 0.110 inch, of blade shank 14 at point 34 where it emerges from member 20. (This configuration provides maximum strength in the relationship of intermediate member 20 to blade 12 at their intersection.) Smoothly sloped surface 36 between hemisphere 32 and annular surface 30 facilitates movement of the instrument through constricted passages, e.g. within the body.

Proximal to head portion 28, member 20 has a smaller diameter, typically about 0.135 inch, for entry into the handle opening, and has an attachment fitting comprising external threads 38 defined on its surface. Proximal shank portion 18 of blade 12, extending axially beneath threads 38, completely through member 20, has surface irregularities in the form of projections or scallops 40 along both side surfaces 42, 44 to create an elongated load-transferring interface 46 between member 20 and the metal blade shank. Shank portion 18 also serves to strengthen the threaded section of the member. Distally of scallops 40, flanges 48 extend from shank 14 transversely to blade axis, A, into the body of member 20 to further secure blade 12 against relative movement within member 20. (The flanges are also understood to provide some slight additional load-transferring between the blade and member.)

Referring now to FIG. 2, a different surgical blade unit 10' is shown with meniscus surgical blade 12' having shank 14' and sharpened blade edge 16'. The member 20 and proximal shank portion (not shown) of the blade unit 10' are identical to that of device 10 shown in FIG. 1. The overall length of this blade is typically about 2.07 inches.

In FIG. 2, device 10' is shown partially threaded into handle 22 which is a hollow rod with an axially aligned blade-receiving opening 50 having internal threads 52 sized and configured to securely receive threaded portion 38 of member 20 over a length, L, typically about 0.27 inch, equal to at least three times the root diameter of member 20 in the area of the threads in order to establish a load-transferring relationship between the handle and the member, and also to ensure that the desired secure connection between the blade unit 10' and handle 22 is achieved. (Only the threaded portion of handle 22 is shown as the blade unit is adapted for attachment to any form of manipulative device having a suitable coacting attachment means.)

Figure 2A:
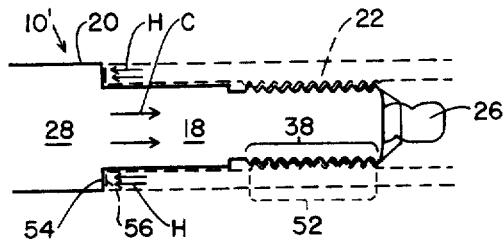
FIGS. 2a and 2b are free body diagrams showing the forces generated in the blade unit locking feature of the invention and FIG. 2c is a graph of tension in the member over length L when the blade is locked in the handle.
Figure 2B:
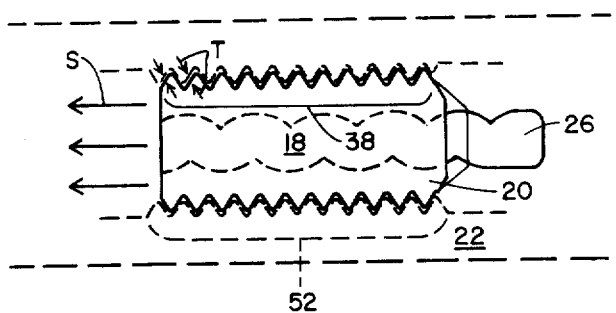

After device 10' is threaded into handle threads 52 the predetermined length L, proximally directed annular butt surface 54 of head portion 28 of member 20 engages upon the distal end surface 56 of handle 22. Referring also to the free body diagrams shown in FIGS. 2a and 2b, slight further relative rotation of blade unit 10', shown in solid line, in handle 22, shown in dashed line, causes the relatively fixed threads 38 of member 20 to resiliently deform slightly between the threads 52 of metal handle 22, without disturbing the load-transferring relationship of member 20 with shank 14'.

Figure 2C:
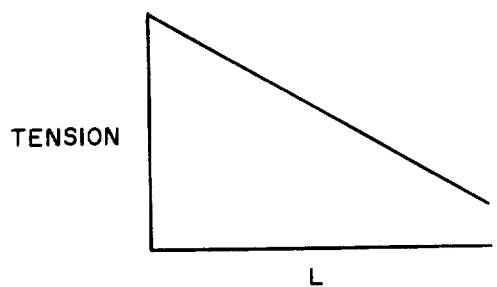

Hand tightening of blade unit 10' on handle 22 generates force, H, due to the resultant compressional engagement of annular butt surface 54 of member 20 on distal end surface 56 of handle 22, and force, C, caused by the rotation of member threads 38 in the proximal direction in relatively fixed threads 52 of handle 22. Coaction of the forces causes resilient stretching of the body of member 20 between the butt surface 54 and the external threads 38 which causes tension in threads 38 and produces a locking frictional relationship between threads 38 of member 20 and the internal threads 52 of handle 22. The opposing forces exerted by the threads, shown representatively in FIG. 2b by arrows T, resist rotation of the blade unit during surgical use. As shown in FIG. 2c, the tension in threads 38 of member 20 decreases in the proximal direction over length L when the blade is locked in the handle.

OPERATION

Figure 3:
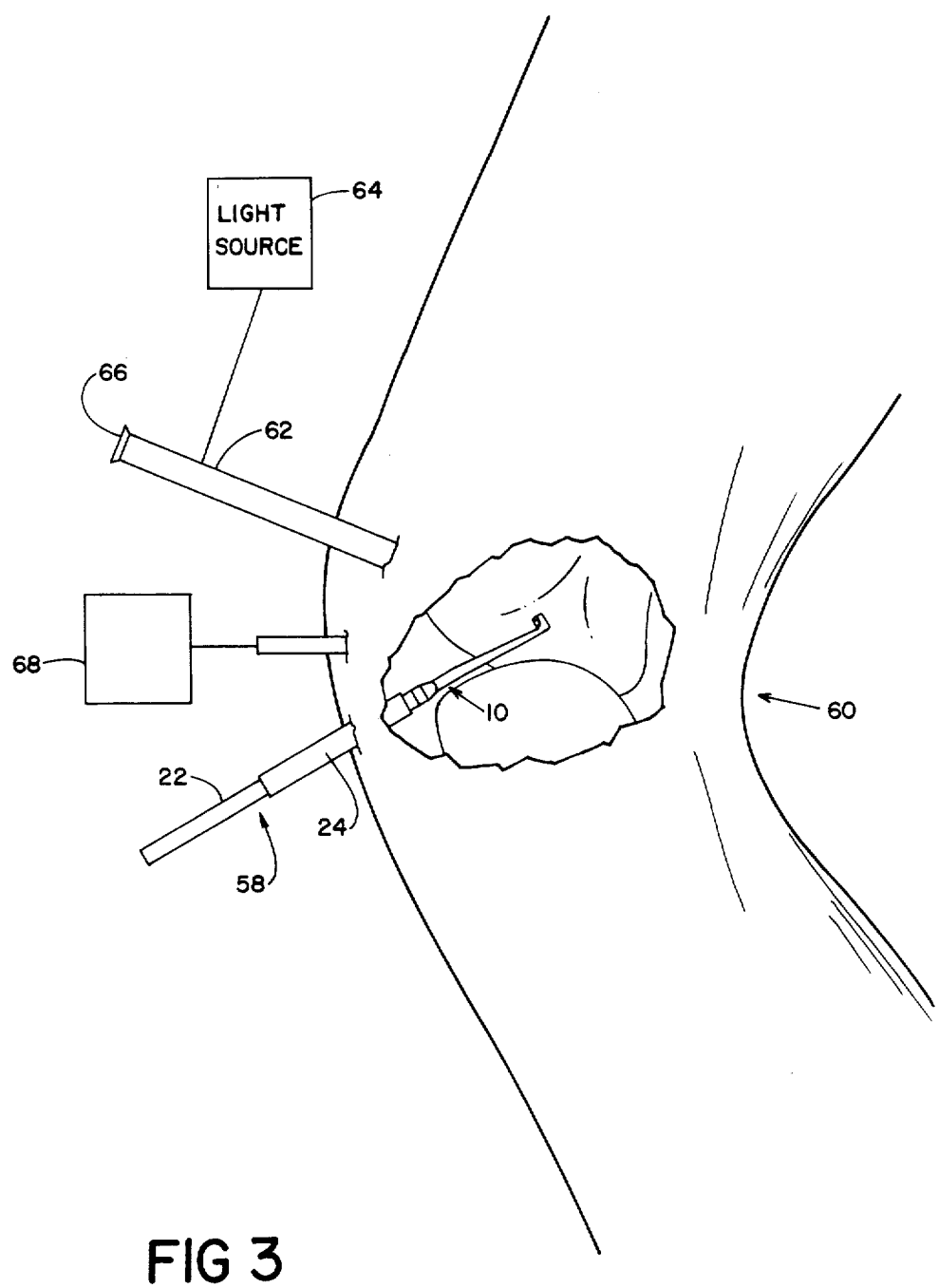
FIG. 3 is a diagrammatic view showing an instrument according to the invention with accessories for arthroscopic surgery of the knee.

Referring now to FIG. 3, surgical instrument 58 with surgical blade unit 10 is shown inserted on the end of handle 22 through narrow cannula 24 into the patient's knee joint 60. At the same time, a fiber optic device 62 introduces light to the interior of the joint from light source 64 and returns a visual image along a separate optical path. The image, in the preferred embodiment shown, is directed to an eyepiece 66 through which the surgeon observes to control his or her movements. (The image can also be recorded or can be directed to a television screen.) During the operation the knee is typically inflated by gas or fluid from source 68.

During the operative procedure, the patient may be anesthesized and punctures made with a trocarring cannula at points about the joint for introduction of the fiber optic device 62, the cannula 24 for instrument 58, and the inflation source 68.

The surgical nurse opens a sealed, sterile package containing a sterile holder 70 (FIG. 4) and surgical blade unit 10" having a blade with a standard side-facing working edge 16" and dumps the holder and blade unit onto a sterile field. The blade unit 10" is then assembled with a handle, which typically has been sterilized by autoclaving and hand tightened until blade unit 10" is locked onto the handle 22.

Referring back to FIG. 3, the instrument is inserted through cannula 24 into knee joint 60. The surgeon positions the retrograde blade with the sharpened edge 16 beyond the tissue he wishes to cut, e.g. cartilage within the knee. The bullet-shaped head portion 28 of blade unit 10 facilitates positioning as it eases the enlarged handle portion into more constricted areas of the joint. Furthermore, by selection of special low friction polymers for the member, e.g. Celcon ® acetal copolymer supplied by Celanese Plastics Materials Co. of Chatham, NJ, Delrin ® acetal polymer supplied by E. I. DuPont de Nemours & Co. of Wilmington, Del., the head portion moves more easily, e.g. than metal, through the tissue.

Referring also to FIG. 5, once the cutting edge is positioned relative to the tissue to be cut (not shown), the surgeon draws instrument 58 proximally, shown representatively by dashed arrows D, to move sharpened edge 16 through the tissue. By cutting in the proximal direction, force R, shown by dashed arrows, is exerted in the distal direction to urge cutting blade unit 10 out of handle 22. This is a critical point of failure for standard metal collets and other collets not having the features of the subject unit, i.e. an intermediate member to transfer the opposing loads between the handle and the metal blade, the forces being shown representatively in FIG. 5 by solid arrows.

The load generated by drawing forces D applied by the surgeon to handle 22 is transferred into member 20, the intermediate member, through the load-transferring relationship established between internal handle threads 52 and external member threads 38. The load of force D, carried through the body of member 20, is then transferred into shank proximal portion 18 of blade 12 through the elongated load-transferring interface 46 between the member 20 and the shank, and finally through metal blade shank 14 to cutting edge 16, to overcome the load of resistance force R, transferred from cutting edge 16 to handle 22 by the same means operating in the opposite direction. Referring to FIG. 5a, any axial movement of proximal portion 18 of shank 14 within member 20 requires that the material of the member expand laterally in the area of threads 38 to allow passage of projecting scallops 30. However, when the blade unit is assembled with a handle, the tightly confining inner surface of handle 22 restricts lateral expansion of the member to further prevent separation of the blade from the handle. Also, the closeness of the projections to the outer surface of member 20 in the area of the threads prevents any significant inward deflection of the threads due to the compressional or resistance forces applied.

In tests, sterilized instruments of this design have withstood opposing forces of up to 50 pounds.

Also, while only retrograde blades (and also surgical hooks and saws) have configurations in which high distal draw-out forces are repeatedly applied, blades with side and end cutting edges, e.g. as shown in FIGS. 2 and 4, may also become wedged or jammed and may have to withstand considerable forces in the distal direction while the surgeon attempts to dislodge them.

After surgery is complete and the severed tissue fragments have been removed from the joint, the cannulas and other instruments are removed and the punctures closed.

MANUFACTURE

Referring now to FIG. 6, the surgical blade unit is manufactured by placing a formed metal blade 12 with the shank proximal portion 18 in the forming cavity 72 defined by mold part 74 and part 76 (FIG. 6a). Cavity 72 has first and second ports, 78 and 80 respectively. Port 78 is sized and adapted to tightly engage about the intermediate portion of shank 14 to form a substantially leak-proof seal. Port 78 also aligns blade 12 along axis A of the device. Port 80 is sized and adapted for connection of injection source 82 of the desired polymeric material to cavity 72. The proximal end portion 26 of shank 14 lies adjacent to port 80.

Mold insert 84, shown also in FIG. 6a, extends between mold parts 74, 76 through the corresponding indent 86 defined in the side surface 42 of shank proximal end 26. The surface of end defining indent 86 engages about insert 84 to resist movement of the blade 12 in the axial direction with the flow of synthetic resin from injection source 82.

The synthetic resin material is selected to have the characteristics of being injection moldable, having good tensile and shear strength at the load transferring interface 46 between the member 20 and the scallops 40 and at the threads 38, 52 (for Celcon ® M90 material, tensile strength is 13,700, 8,000, and 5,000 lbs./in.$^2$ at $-40°$ F., 73° F. and 160° F. respectively; and shear strength is 7,700, 6,700 and 5,700 lbs./in.$^2$ at 73° F., 120° F. and 160° F., respectively), being compressible under hand pressure (the compressive stress of Celcon ® M90 is 4500 lb./in.$^2$ at 1% deflection and 16,000 lb./in.$^2$ at 10% deflection), and generating tight friction with the opposed threads of the handle for locking the blade into the handle.

For insertion into the body, the material must be FDA approved, and be sterilizable, e.g. by autoclaving or irradiation, and also, for easy movement through constricted openings in the tissue, the material should have the characteristic of low surface friction. Forms of nylon, acetal copolymer, polysulfone, polyethylene and polypropylene polymers have these characteristics.

Mold part 88 is positioned about the distal end of blade 12 to further align the blade in the mold cavity and also provide an abutting surface 90 to further prevent axial movement of blade 12 with the flow of synthetic resin into the cavity.

After the blade 12 is positioned in the mold, the mold parts are closed under pressure and the mold parts lock blade 12 in position. Synthetic resin material is injected from source 82 in liquid form at high pressure through port 80 to fill cavity 72.

As the synthetic resin in cavity 72 cools, it permanently contracts about shank 14 of blade 12 forming load transferring interface 46 and exerting hoop-tension forces to hold the shank 14 tightly within the molded member 20. When the resin has sufficiently cooled, the mold is opened and the surgical blade unit 10 of blade 12 and member 20 is ejected.

OTHER EMBODIMENTS

Other embodiments of the invention are within the following claims. For example, other surgical blade units, e.g. surgical hooks or saws, may be fitted with a member according to the invention for securing to a handle. The blade blank can have other forms, e.g. round. The blade units may be provided in sterile or non-sterile packaging. Also, mold parts corresponding to part 78 shown in FIG. 6 may be used with other configurations to perform the same purpose. Also, because the sharpened edge is positioned outside the mold during the operation, the blades may be presharpened prior to molding. In some blade configurations, e.g. the retrograde and meniscus blades (12, FIG. 1; 12' FIG. 2, respectively), the edge is protected by adjacent masses of the blade. In other configurations, e.g. as shown in FIG. 4, the edge should be protected, e.g. with a piece of soft tubing. The attachment fitting of the blade unit to the handle may be achieved by other means, e.g. without the tensioned-thread locking feature of the preferred embodiment described above.

We claim:

1. A surgical blade unit for receiving substantial cutting load and adapted for use with a selected shaft-form handle that has, at its distal end, an axially aligned blade-unit receiving opening, said blade unit comprising:
  (a) a metal blade defining a working edge and a load-transmitting, axially elongated metal support shank extending from said edge, and
  (b) an intermediate load-transferring member of synthetic resin permanently molded about a proximal portion of said shank, the distal extremity of said intermediate member being spaced proximally from said working edge leaving said blade and a substantial length of the distal portion of said shank exposed, a proximal portion of said intermediate member defining an attachment fitting adapted to engage in load-transferring relationship with said handle, the proximal portion of said shank extending through the intermediate member substantially into the region of said attachment fitting and being permanently embedded within said intermediate molded member to define an elongated, load-transferring interface therewith, said intermediate member being comprised of synthetic resin that has substantial tensile and shear strength and being constructed and arranged to receive via said attachment fitting the surgeon's forces on said handle, and to receive via said substantial load-transferring interface, forces from said proximal end of said shank attributable to the resistance encountered by said metal blade, the substance of said intermediate member adapted to transfer said surgeon's forces to overcome said resistance forces while maintaining said blade in fixed relationship to said handle.

2. A surgical blade unit for receiving substantial cutting load and adapted for use with a selected shaft-form handle that has, at its distal end, an axially aligned, internally threaded blade-unit receiving opening, said blade unit comprising:
  (a) a metal blade defining a working edge and a load-transmitting, axially elongated metal support shank extending from said edge,
  (b) an intermediate load-transferring member of synthetic resin permanently molded about a proximal portion of said shank, the distal extremity of said intermediate member being spaced proximally from said working edge leaving said blade and a substantial length of the distal portion of said shank exposed, a distal portion of said intermediate member being terminated in a proximally directed, annular butt surface adapted to engage a distally directed surface of said handle, and a proximal portion of said intermediate member having a smaller diameter than said distal portion and defining an attachment fitting on its surface comprising a set of external threads adapted to match and engage in load-transferring relationship with internal threads of said handle, the proximal portion of said shank extending through the intermediate member in the region of said attachment fitting and being permanently embedded within said intermediate molded member to define an elongated, load-transferring interface therewith, said intermediate member being comprised of synthetic resin that has substantial tensile and shear strength and being constructed and arranged to receive via said attachment fitting the surgeon's forces on said handle, and to receive via said substantial load-transferring interface, forces from said proximal end of said shank attributable to the resistance encountered by said metal blade, the substance of said intermediate member adapted to transfer said surgeon's forces to overcome said resistance forces while maintaining said blade in fixed relationship to said handle.

3. The surgical blade unit of claim 2 wherein the body of said intermediate member is resiliently deformable to the degree that, without disturbing the load-transferring relationship of said intermediate member with said shank, hand tightening of the threads of said blade unit on said handle, and resultant compressional engagement of said annular butt surface of said intermediate member with the distal end surface of said handle, causes resilient stretching of the body of said intermediate member between said butt-surface and said external threads to produce a locking frictional engagement between said thread and the internal threads of said handle thereby to prevent rotation of said blade unit during surgical use.

4. The surgical blade unit of claim 1 or 2 wherein said blade unit is in the form of an arthroscopic blade, said blade and intermediate member being sized to lie within a surgical cannula.

5. The surgical blade unit of claim 1 or 2 wherein said blade unit is a retrograde blade,
  the working edge of said blade unit being disposed for operation during reverse cutting.

6. A surgical blade unit for receiving substantial cutting load and adapted for use in arthroscopic surgery with a selected shaft-form handle that has, at its distal end, an axially aligned, internally threaded blade-unit receiving opening,
  said blade unit being sized to lie within a surgical cannula and comprising:
    (a) a metal retrograde blade defining a working edge disposed for operation during reverse cutting and a load-transmitting, axially elongated metal support shank extending from said edge, (b) an intermediate load-transferring member of synthetic resin permanently molded about a proximal portion of said shank, the distal extremity of said intermediate member being spaced proximally from said working edge leaving said blade and a substantial length of the distal portion of said shank exposed, a distal portion of said intermediate member being terminated in a proximally directed, annular butt surface adapted to engage a distally directed surface of said handle, and a proximal portion of said intermediate member having a smaller diameter than said distal portion and defining an attachment fitting on its surface comprising a set of external threads adapted to match and engage in load-transferring relationship with internal threads of said handle, the proximal portion of said shank extending through the intermediate member in the region of said attachment fitting and being permanently embedded within said intermediate molded member to define an elongated, load-transferring interface therewith, said intermediate member being comprised of synthetic resin that has substantial tensile and shear strength and being constructed and arranged to receive via said attachment fitting the surgeon's forces on said handle, and to receive via said substantial load-transferring interface, forces from said proximal end of said shank attributable to the resistance encountered by said metal blade, the substance of said intermediate member adapted to transfer said surgeon's forces to overcome said resistance forces while maintaining said blade in fixed relationship to said handle, the body of said intermediate member being resiliently deformable to the degree that, without disturbing the load-transferring relationship of said intermediate member with said shank, hand tightening of the threads of said blade unit on said handle, and resultant compressional engagement of said annular butt surface of said intermediate member with the distal end surface of said handle, causes resilient stretching of the body of said intermediate member between said butt-surface and said external threads to produce a locking frictional engagement between said thread and the internal threads of said handle thereby to prevent rotation of said blade unit during surgical use.

7. The surgical blade unit of claim 1, 2 or 6 assembled with a selected shaft-form handle, the blade-unit receiving opening of said handle being configured to receive the attachment fitting portion of said blade unit in a close-fitting relationship, whereby said intermediate member is restricted against lateral expansion by the confining surfaces defining said opening.

8. The surgical blade unit of claim 1, 2 or 6 wherein said synthetic resin is sterilizable.

9. The surgical blade unit of claim 8 wherein said synthetic resin is selected from the group consisting of nylon, acetal, polysulfone, polyethylene and polypropylene.

10. The surgical blade unit of claim 1, 2 or 6 wherein the distal end of said intermediate member is tapered to facilitate entry of said blade unit between close-lying portions of the body during surgery.

11. A surgical blade unit for receiving substantial cutting load and adapted for use under high forces in arthroscopic surgery with a selected shaft-form handle that has, at its distal end, an axially aligned, internally threaded blade-unit receiving opening, said blade unit being sized to lie within a surgical cannula and comprising:

(a) a metal retrograde blade defining a working edge disposed for operation during reverse cutting and a load-transmitting, axially elongated metal support shank extending from said edge, (b) an intermediate load-transferring member of synthetic resin permanently molded about a proximal portion of said shank, a proximal portion of said intermediate member defining an attachment fitting adapted to engage in load-transferring relationship with said handle, the proximal portion of said shank extending through the intermediate member substantially into the region of said attachment fitting and being permanently embedded within said intermediate molded member to define an elongated, load-transferring interface therewith, and the distal extremity of said intermediate member being spaced proximally from said working edge leaving said blade and a substantial length of the distal portion of said shank exposed, at the distal extremity of said intermediate member, said shank and said member being substantially coaxial, the distal extremity of said shank supporting said working edge disposed for reverse cutting being substantially coaxial with said intermediate member, and the intervening exposed distal portion of said shank lying on an axis at an angle transverse to the axis of said intermediate member, said intermediate member being comprised of synthetic resin that has substantial tensile and shear strength and being constructed and arranged to receive via said attachment fitting the surgeon's forces on said handle, and to receive via said substantial load-transferring interface, forces from said proximal end of said shank attributable to the resistance encountered by said metal blade, the substance of said intermediate member adapted to transfer said surgeon's forces to overcome said resistance forces while maintaining said blade in fixed relationship to said handle.

* * * * *